(12) United States Patent
Gopalan et al.

(10) Patent No.: US 10,832,590 B2
(45) Date of Patent: Nov. 10, 2020

(54) MONITORING FOOD INTAKE

(71) Applicant: AT&T Intellectual Property I, L.P., Atlanta, GA (US)

(72) Inventors: Raghuraman Gopalan, Dublin, CA (US); Eric Zavesky, Austin, TX (US); Bernard S. Renger, New Providence, NJ (US); Zhu Liu, Marlboro, NJ (US); Behzad Shahraray, Holmdel, NJ (US); David Crawford Gibbon, Lincroft, NJ (US); Lee Begeja, Gillette, NJ (US); Paul Triantafyllou, Watchung, NJ (US); Tan Xu, Bridgewater, NJ (US)

(73) Assignee: AT&T INTELLECTUAL PROPERTY I, L.P., Atlanta, GA (US)

( * ) Notice: Subject to any disclaimer, the term of this patent is extended or adjusted under 35 U.S.C. 154(b) by 0 days.

(21) Appl. No.: 15/703,641

(22) Filed: Sep. 13, 2017

(65) Prior Publication Data

US 2019/0080629 A1   Mar. 14, 2019

(51) Int. Cl.
| | |
|---|---|
| G09B 19/00 | (2006.01) |
| G06F 19/00 | (2018.01) |
| G06K 9/46 | (2006.01) |
| G06K 9/00 | (2006.01) |
| G16H 20/60 | (2018.01) |
| G16H 40/63 | (2018.01) |

(52) U.S. Cl.
CPC ..... *G09B 19/0092* (2013.01); *G06F 19/3475* (2013.01); *G06K 9/00671* (2013.01); *G06K 9/46* (2013.01); *G16H 20/60* (2018.01); *G16H 40/63* (2018.01); *G06K 2209/17* (2013.01); *G06T 2207/30128* (2013.01)

(58) Field of Classification Search
CPC .. G09B 19/0092; G06K 9/46; G06K 2209/17; G06F 19/3475; G06T 2207/30128
USPC .......................................................... 382/176
See application file for complete search history.

(56) References Cited

U.S. PATENT DOCUMENTS

| | | | |
|---|---|---|---|
| 8,712,108 B2 | 4/2014 | Miyahara et al. | |
| 8,715,181 B2 | 5/2014 | Brynelsen et al. | |
| 9,536,449 B2 | 1/2017 | Connor | |
| 9,773,427 B2 | 9/2017 | Ghalavand | |
| 2013/0289886 A1 | 10/2013 | Ricks | |
| 2014/0303790 A1* | 10/2014 | Huang | G06Q 50/22 700/281 |

(Continued)

OTHER PUBLICATIONS

Mirtchouk, Mark, Christopher Merck, and Samantha Kleinberg. "Automated estimation of food type and amount consumed from body-worn audio and motion sensors." Proceedings of the 2016 ACM International Joint Conference on Pervasive and Ubiquitous Computing. 2016. (Year: 2016).*

(Continued)

*Primary Examiner* — Amandeep Saini

(57) ABSTRACT

In one example, the present disclosure describes a device, computer-readable medium, and method for monitoring a user's food intake. For instance, in one example, a user's food intake is monitored based on data collected from a sensor. The user's current nutrient consumption is estimated based on the monitoring. A recommendation is presented to the user based on the estimating, where the recommendation is designed to help the user achieve a target nutrient consumption.

20 Claims, 4 Drawing Sheets

(56) References Cited

U.S. PATENT DOCUMENTS

| | | | |
|---|---|---|---|
| 2014/0334691 A1* | 11/2014 | Cho | G06Q 30/0631 |
| | | | 382/110 |
| 2015/0260699 A1* | 9/2015 | Minvielle | A47J 27/04 |
| | | | 426/231 |
| 2016/0071423 A1* | 3/2016 | Sales | A61B 5/1103 |
| | | | 434/127 |
| 2016/0073953 A1 | 3/2016 | Sazonov | |
| 2016/0132642 A1 | 5/2016 | Carmi | |
| 2016/0143582 A1 | 5/2016 | Connor | |
| 2016/0148535 A1* | 5/2016 | Ashby | A61B 7/008 |
| | | | 434/127 |
| 2016/0150213 A1* | 5/2016 | Mutti | G06K 9/4604 |
| | | | 348/143 |
| 2016/0270717 A1 | 9/2016 | Luna et al. | |
| 2016/0350514 A1* | 12/2016 | Rajendran | G16H 20/60 |
| 2017/0061821 A1 | 3/2017 | Choi et al. | |
| 2017/0220772 A1 | 8/2017 | Vleugels et al. | |
| 2017/0270820 A1 | 9/2017 | Ashby | |
| 2017/0286625 A1* | 10/2017 | Blander | A61B 5/0245 |
| 2017/0340147 A1* | 11/2017 | Hambrock | G01F 23/263 |

OTHER PUBLICATIONS

Haik Kalantarian et al., "A wearable nutrition monitoring system", Wearable and Implantable Body Sensor Networks (BSN), 2014 11th International Conference on IEEE (2014). pp. 75-80.

Oliver Amft et al., "On-body sensing solutions for automatic dietary monitoring", IEEE pervasive computing vol. 8, Issue 2 (2009). 10 Pages.

* cited by examiner

US 10,832,590 B2

MONITORING FOOD INTAKE

The present disclosure relates generally to automated assistance, and relates more particularly to devices, non-transitory computer-readable media, and methods for monitoring a user's food intake.

BACKGROUND

People are paying greater attention to what they eat. Some people may be motivated to monitor their eating habits in order to lose weight or improve athletic performance. Others may be motivated by a desire to manage other aspects of their health that are connected to their eating habits (e.g., to lower blood pressure, control diabetes symptoms, avoid allergens, etc.).

SUMMARY

In one example, the present disclosure describes a device, computer-readable medium, and method for monitoring a user's food intake. For instance, in one example, a user's food intake is monitored based on data collected from a sensor. The user's current nutrient consumption is estimated based on the monitoring. A recommendation is presented to the user based on the estimating, where the recommendation is designed to help the user achieve a target nutrient consumption.

In another example, a device includes a processor and a computer-readable medium storing instructions which, when executed by the processor, cause the processor to perform operations. The operations include monitoring a food intake of a user based on data collected from a sensor, estimating a current nutrient consumption of the user based on the monitoring, and presenting a recommendation to the user based on the estimating, wherein the recommendation is designed to help the user achieve a target nutrient consumption.

In another example, an apparatus includes a sensor to detect information about a food item placed in the apparatus, a processor to evaluate the information detected by the sensor and to make a decision regarding the food item, based on the information, and a user interface to present a recommendation to a user regarding preparation of the food item by the apparatus.

BRIEF DESCRIPTION OF THE DRAWINGS

The teachings of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

In one example, the present disclosure monitors a user's eating habits and provides feedback to the user to encourage the consumption of optimal nutrients. As discussed above, people are paying greater attention to what they eat. However, this does not mean that it is always easy to make the best eating choices. Poor eating habits can still develop consciously or unconsciously.

Examples of the present disclosure leverage the availability and versatility of mobile communications devices and sensors to monitor a user's eating habits and to provide feedback, when appropriate, to help the user develop eating habits that will result in the consumption of optimal nutrients. What is considered "optimal" in terms of nutritional goals may be personalized for the user; for instance, one user may wish to increase his intake of carbohydrates to enhance athletic performance, while another user may wish to decrease his sodium intake to reduce blood pressure. Sensors for monitoring food intake may be attached to food packaging (e.g., box, wrapper, etc.), to items used to consume food (e.g., plates, cups, utensils, etc.), to items used to prepare the food (e.g., oven or microwave oven, blender, etc.), to the user's mobile devices (e.g., mobile phone, smart watch, fitness tracker, etc.), and/or to items, appliances, or structures located in the surrounding environment (e.g., scale, ceiling, etc.). These sensors may transmit collected data regarding the user's food intake to a central server or computing device that can aggregate the data.

Feedback may be provided via the user's mobile device(s) (e.g., mobile phone, smart watch, fitness tracker, etc.). The feedback may take the form of an audible or visible alert (e.g., a text message or application-based alert sent to the user's mobile phone). The feedback may present a detailed report on the user's food intake progress (e.g., quantity of calories, vitamins, and/or other nutrients consumed over a window of time). The feedback may also present suggestions for achieving the consumption of optimal nutrients (e.g., nutrients and/or foods that the user can consume to make progress toward a goal). The feedback may also present advertising and/or mechanisms for obtaining suggested nutrients or foods (e.g., advertisements, coupons, or hyperlinks through which the nutrients or foods can be purchased).

Figure 1:
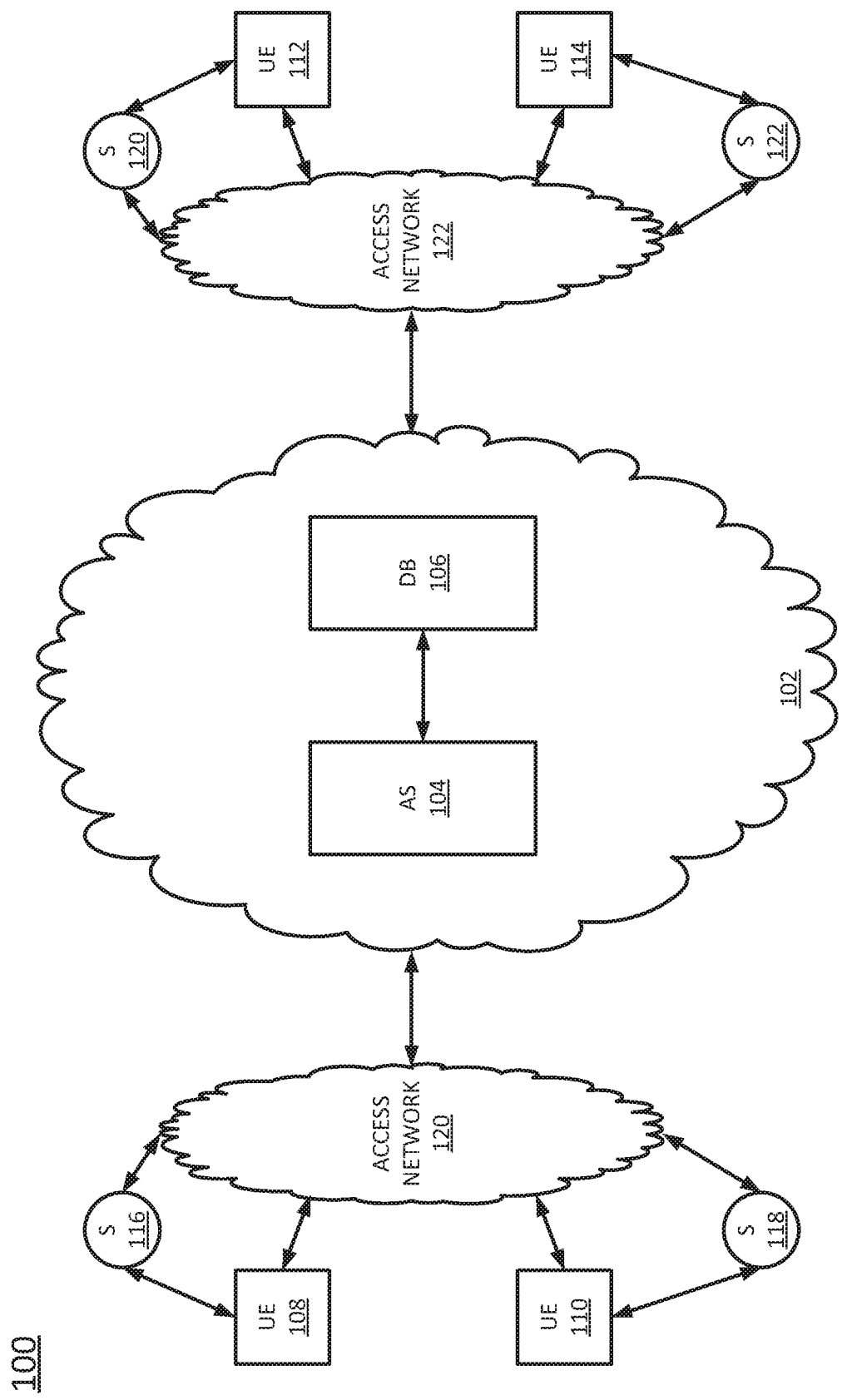
FIG. 1 illustrates an example network related to the present disclosure.

To better understand the present disclosure, FIG. 1 illustrates an example network 100, related to the present disclosure. The network 100 may be any type of communications network, such as for example, a traditional circuit switched network (CS) (e.g., a public switched telephone network (PSTN)) or an Internet Protocol (IP) network (e.g., an IP Multimedia Subsystem (IMS) network, an asynchronous transfer mode (ATM) network, a wireless network, a cellular network (e.g., 2G, 3G and the like), a long term evolution (LTE) network, and the like) related to the current disclosure. It should be noted that an IP network is broadly defined as a network that uses Internet Protocol to exchange data packets. Additional exemplary IP networks include Voice over IP (VoIP) networks, Service over IP (SoIP) networks, and the like.

In one example, the network 100 may comprise a core network 102. In one example, core network 102 may functionally comprise a fixed mobile convergence (FMC) network, e.g., an IP Multimedia Subsystem (IMS) network. In addition, core network 102 may functionally comprise a telephony network, e.g., an Internet Protocol/Multi-Protocol Label Switching (IP/MPLS) backbone network utilizing Session Initiation Protocol (SIP) for circuit-switched and Voice over Internet Protocol (VoIP) telephony services. Core network 102 may also further comprise an Internet Service Provider (ISP) network. In one example, the core network 102 may include an application server (AS) 104 and a database (DB) 106. Although only a single AS 104 and a single DB 106 are illustrated, it should be noted that any number of application servers 104 or databases 106 may be deployed. Furthermore, for ease of illustration, various additional elements of core network 102 are omitted from FIG. 1.

Figure 4:
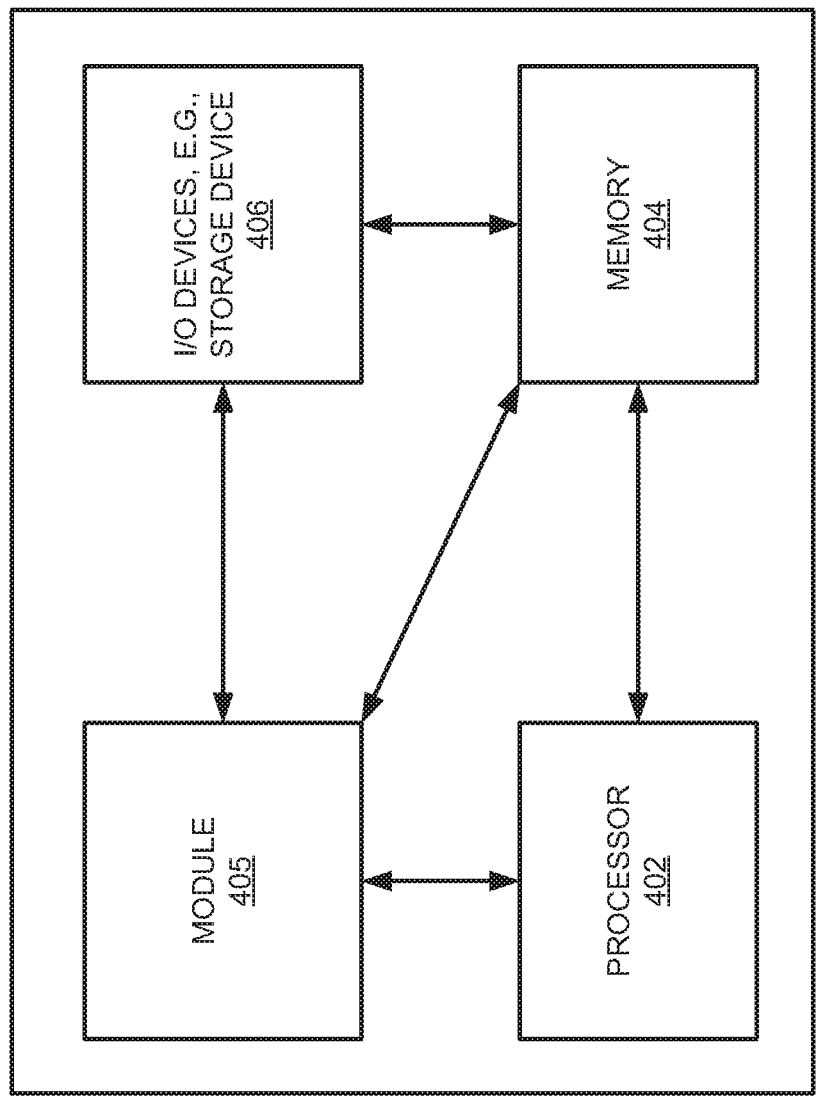
FIG. 4 depicts a high-level block diagram of a computing device specifically programmed to perform the functions described herein.

In one example, the AS 104 may comprise a general purpose computer configured as a special-purpose computer, as illustrated in FIG. 4 and discussed below. In one example, the AS 104 may perform the methods discussed below related to providing monitoring a user's food intake and providing feedback. For instance, the AS 104 may aggregate data provided by a plurality of sensors to determine a user's current food intake, estimate the nutrients consumed via the current food intake, compare the estimate nutrients to a target nutrient consumption, and make a recommendation for additional food intake to achieve the target nutrient consumption.

In one example, the DB 106 may store data relating to nutrition and/or to user nutritional goals. For example, the DB 106 may store user profiles, which users can update dynamically at any time in order to indicate nutritional goals or preferences (e.g., avoid sugar, keep daily calorie consumption below x calories, etc.). These nutritional goals or preferences could also be stored in the form of a personalized nutritional plan (e.g., foods recommended for the user by a doctor or nutritionist). The user profiles may also include relevant user history information (e.g., historical eating habits, history of feedback sent to user regarding suggested food intake, measurements of weight, blood pressure, or other health-related metrics, etc.). User profiles may be stored in encrypted form to protect user privacy.

Other nutrition-related data stored by the DB 106 may include general lists of recommended (e.g. "healthy") foods, anonymized eating patterns, and/or data about specific types of diets (e.g., gluten-free, vegan, low-sodium, sports-specific diets, etc.). At least some of this nutrition-related data could originate with doctors, nutritionists, academic research, or government or private health organizations (e.g., the National Institutes of Health, the Food and Drug Administration, etc.).

The core network 102 may be in communication with one or more wireless access networks 120 and 122. Either or both of the access networks 120 and 122 may include a radio access network implementing such technologies as: global system for mobile communication (GSM), e.g., a base station subsystem (BSS), or IS-95, a universal mobile telecommunications system (UMTS) network employing wideband code division multiple access (WCDMA), or a CDMA3000 network, among others. In other words, either or both of the access networks 120 and 122 may comprise an access network in accordance with any "second generation" (2G), "third generation" (3G), "fourth generation" (4G), Long Term Evolution (LTE), or any other yet to be developed future wireless/cellular network technology including "fifth generation" (5G) and further generations. The operator of core network 102 may provide a data service to subscribers via access networks 120 and 122. In one example, the access networks 120 and 122 may all be different types of access networks, may all be the same type of access network, or some access networks may be the same type of access network and other may be different types of access networks. The core network 102 and the access networks 120 and 122 may be operated by different service providers, the same service provider or a combination thereof.

In one example, the access network 120 may be in communication with one or more user endpoint devices (also referred to as "endpoint devices" or "UE") 108 and 110, while the access network 122 may be in communication with one or more user endpoint devices 112 and 114. Access networks 120 and 122 may transmit and receive communications between respective UEs 108, 110, 112, and 124 and core network 102 relating to communications with web servers, AS 104, and/or other servers via the Internet and/or other networks, and so forth.

In one example, the user endpoint devices 108, 110, 112, and 114 may be any type of subscriber/customer endpoint device configured for wireless communication such as a laptop computer, a Wi-Fi device, a Personal Digital Assistant (PDA), a mobile phone, a smartphone, an email device, a computing tablet, a messaging device, a wearable smart device (e.g., a smart watch or fitness tracker), a portable media device (e.g., an MP3 player), a gaming console, a portable gaming device, and the like. In another example, the user endpoint device may be a smart appliance (i.e., a home appliance having processing and/or communication capabilities), such as a microwave oven, a refrigerator, a thermostat, or the like. In one example, any one or more of the user endpoint devices 108, 110, 112, and 114 may have both cellular and non-cellular access capabilities and may further have wired communication and networking capabilities. It should be noted that although only four user endpoint devices are illustrated in FIG. 1, any number of user endpoint devices may be deployed.

In addition, the network 100 may also comprise a plurality of sensors 116, 118, 120, and 122. The sensors 116, 118, 120, and 122 may be affixed, for example, to food packaging (e.g., box, wrapper, etc.), to items used to consume food (e.g., plates, cups, utensils, etc.), to items used to store and prepare the food (e.g., refrigerator, oven or microwave oven, blender, etc.), to the user's mobile devices (e.g., user endpoint devices 108, 110, 112, and 114), and/or to items, appliances, or structures located in the surrounding environment (e.g., scale, ceiling, cashier station in a cafeteria or fast food establishment, etc.). The sensors 116, 118, 120, and 122 may collect data about a user's food intake and forward the data to the AS 104 and/or one or more of the user endpoint devices 108, 110, 112, and 114. The sensors 116, 118, 120, and 122 may also communicate and share data with each other. In one example, the sensors 116, 118, 120, and 122 comprise sensors of a plurality of different modalities, such as imaging sensors (e.g., still and/or video cameras, infrared cameras), audio sensors (e.g., transducers or microphones), biometric detectors (e.g., fingerprint detectors, ocular feature detectors, etc.), health monitors (e.g., glucose monitors, heart rate monitors, etc.), thermal sensors (e.g., thermometers), machine readable label scanners (e.g., bar code, quick response, or data matrix scanners), radio frequency (RF) detectors, and other types of sensors.

It should also be noted that as used herein, the terms "configure" and "reconfigure" may refer to programming or loading a computing device with computer-readable/computer-executable instructions, code, and/or programs, e.g., in a memory, which when executed by a processor of the computing device, may cause the computing device to perform various functions. Such terms may also encompass providing variables, data values, tables, objects, or other data structures or the like which may cause a computer device executing computer-readable instructions, code, and/or programs to function differently depending upon the values of the variables or other data structures that are provided. For example, any one or more of the user endpoint devices 108, 110, 112, and 114 may host an operating system for presenting a user interface that may be used to send data to the AS 104 (e.g., updates to user profiles/preferences, sensor readings, etc.) and for reviewing data sent by the AS 104 (e.g., alerts, recommendations, etc.).

Those skilled in the art will realize that the network 100 has been simplified. For example, the network 100 may include other network elements (not shown) such as border elements, routers, switches, policy servers, security devices, a content distribution network (CDN) and the like. The network 100 may also be expanded by including additional endpoint devices, access networks, network elements, application servers, etc. without altering the scope of the present disclosure.

Figure 2:
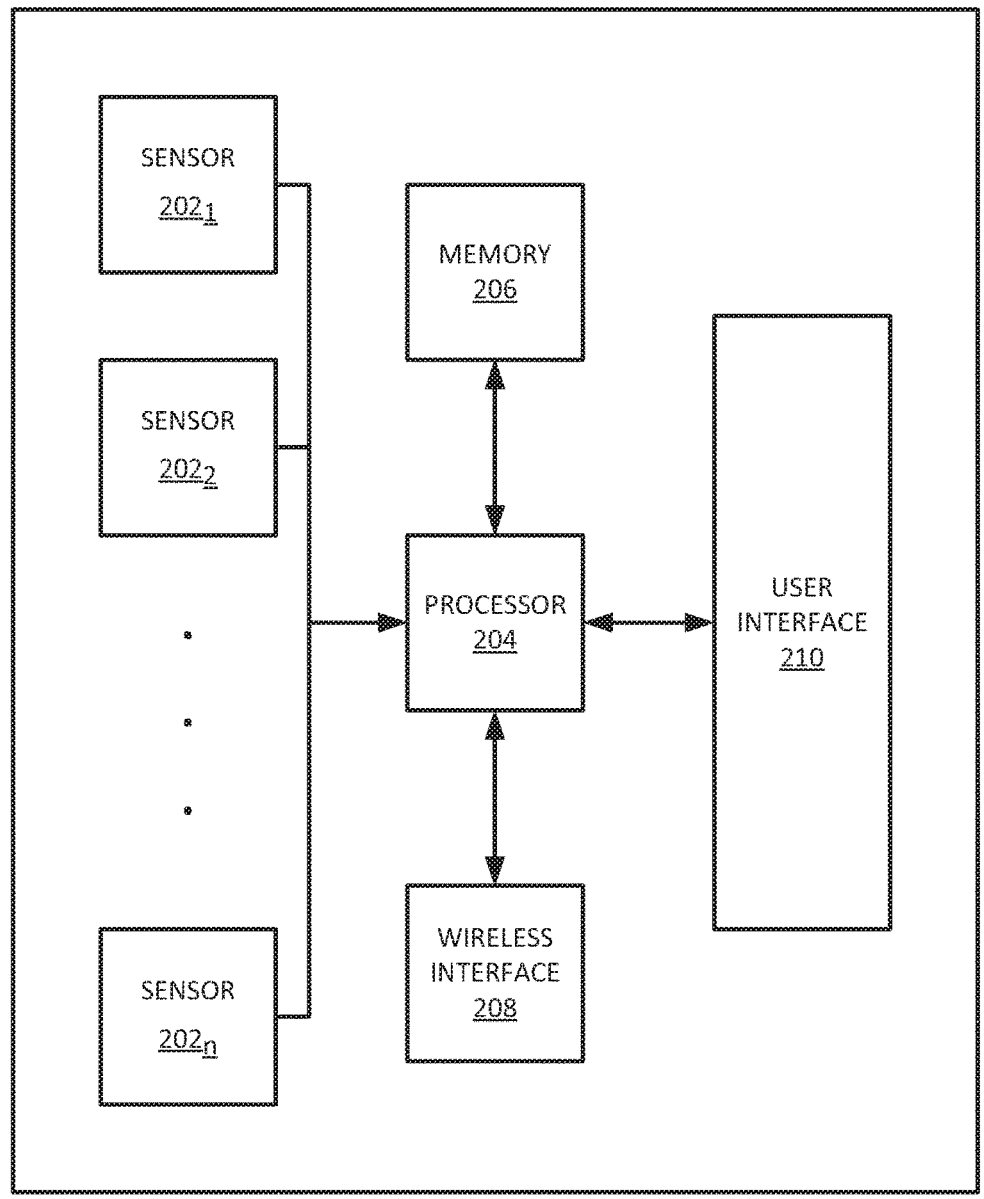
FIG. 2 illustrates a block diagram of an example device for monitoring a user's food intake.

To further aid in understanding the present disclosure, FIG. 2 illustrates a block diagram of an example device 200 for monitoring a user's food intake. In one example, the device 200 is a smart home appliance, which may be one of the user endpoint devices 108, 110, 112, and 114. As an example, the device 200 will be described within the context of a smart microwave oven. However, other types of smart home appliances could be configured similarly, including refrigerators, blenders, ovens, and the like.

The device 200 generally includes a plurality of sensors 2021-202n (hereinafter collectively referred to as "sensors 202"), a processor 204, a memory 206, a wireless interface 208, and a user interface 210.

The sensors 202 may include sensors of a plurality of different modalities, and different types of sensors 202 may be positioned in different locations in and/or around the device 200. For instance, if the device 200 is a microwave oven, the sensors 202 may include one or more imaging sensors (e.g., cameras) mounted on or near the door of the microwave oven, for capturing images of food placed in the microwave oven for cooking. The imaging sensors could include, for example, a set of cameras for performing three-dimensional scanning. The sensors 202 may further include one or more machine readable label scanners (e.g., barcode scanners) or radio frequency identification (RFID) receivers mounted on or near the door of the microwave oven, for scanning machine readable labels or RFID tags on the packaging of food placed in the microwave oven for cooking (e.g., where the machine readable labels may be encoded with information about the food, such as cooking instructions). The sensors 202 may further include one or more pressure sensors mounted on the microwave oven tray, for recording the weight or mass of food placed in the microwave oven for cooking. The sensors 202 may further include one or more temperature sensors positioned inside the microwave oven for monitoring the temperature at which the food is cooked. The sensors 202 may further include one or more acoustic sensors positioned inside the microwave oven to monitor sounds coming from food during cooking (e.g., popping popcorn, sizzling, boiling water, etc.). The sensors 202 may further include one or more humidity sensors positioned inside the microwave oven to monitor the moisture content in food during cooking (e.g., beginning moisture content versus current moisture content versus desired moisture content when fully cooked).

The processor 204 subscribes to the outputs of at least some of the sensors 202. The processor 204 may be programmed to extract data from the outputs of the sensors 202 and to evaluate this data in order to make a decision regarding food with which the device 200 comes into contact. For instance, if the device 200 is a microwave oven, the processor 204 may perform object recognition processing on images captured by sensors 202 positioned one or near the door of the microwave oven. The object recognition processing may result in the identification of a food item that has been placed in the microwave oven for cooking. If the processor is programmed with the ability to perform three-dimensional object reconstruction based on the images, the processor may also be able to estimate the weight, mass, or density of the food item. The processor 204 may further perform processing of readings obtained from a pressure sensor mounted to the microwave oven tray. Processing these readings may result in the determination of the weight or mass of the food item that has been placed in the microwave oven for cooking. The processor 204 may be further configured to perform speech recognition processing when the device 200 includes a user interface 210 with a voice interface. Alternatively, the processor 204 may interact (e.g., via the wireless interface 208) with a remote processor or server that processes the sensor data and forwards any conclusions drawn from the sensor data (e.g., food identification and/or weight, mass, or density) to the processor 204. The remote processor or server may further host a nutrition-related application that can be consulted for tracking the user's current food intake.

The memory 206 may store information regarding different types of food with which the device 200 may come into contact. For instance, if the device 200 is a microwave oven, this information may comprise recommended cooking times based on types and/or quantities of food (where the recommended cooking times may be optimized to prevent food-borne contamination while preserving a maximal amount of nutrients, for example). The memory 206 may also store user preferences regarding different types of food with which the device 200 may come into contact. These user preferences may include feedback provided by a user in response to a recommendation made by the device 200, as described in further detail below. In another example, information regarding types of food and/or user preferences may also be stored remotely, e.g., in a remote database that is accessible via the wireless interface 208.

The user interface 210 comprises one or more input/output devices for interacting with a user. For instance, the user interface 210 may comprise some combination of a display, keypad, speaker, microphone, or the like. In one example, the user interface 210 comprises a touch screen or voice interface. The user interface 210 may be used to present information to the user and also to receive further information and feedback from the user. For instance, if the device 200 is a microwave oven, the user interface 210 may be used to present the user with an estimate as to the type and weight or mass of a food item placed in the microwave oven (e.g., "five ounce potato") and ask the user to confirm this estimate. User feedback (e.g., confirming or disputing the estimate) may be used to improve the processes used to identify food type and quantity. The user interface 210 may also be used to present the user with a query after cooking, to determine whether the food has been undercooked, overcooked, or cooked correctly. The user feedback may not always be so explicit. For example, if the user puts the food back in the microwave oven for additional cooking, this can be interpreted as feedback indicating that the food was undercooked. User feedback to this query may also be used to adjust information regarding recommended cooking times for certain types and quantities of food.

In addition to communicating with remote processors and/or memory for information, the wireless interface 208 could also be programmed to communicate with other smart devices or appliances (e.g., blenders, refrigerators, etc.). This would allow the device 200 to communicate with other devices, for example to convey the status of food being prepared. This could be useful where a recipe calls for the use of multiple appliances; in this case, the appliances can be synchronized to facilitate more efficient preparation of the recipe (e.g., by tracking steps performed, progress, etc.). For instance, a smart oven could be programmed to begin preheating when it knows that a particular recipe is being prepared, and it has received a signal from a smart refrigerator that certain ingredients used in the recipe have been taken out.

In further examples, sensors 202 that are configured to capture identifying data may capture identifying data of the user. For instance, the sensors might include biometric and/or imagining sensors to capture still and/or video images of the user (e.g., images of the user's face, body, or ocular region), sensors to capture the user's fingerprints, a microphone to capture a sample of the user's speech, or other sensors. The processor 204 could be programmed to perform recognition techniques on the identifying data (e.g., facial recognition, iris identification, gait analysis, speech identification, fingerprint identification, etc.) in order to identify the user, allowing for better personalization of the device 200 and its operations. In another example, user identification may be explicitly obtained through communication (e.g., near-field communication) with the user's mobile phone, wearable smart device, or other device. In this case, individualized profiles for multiple users may be accessible by the device 200.

Figure 3:
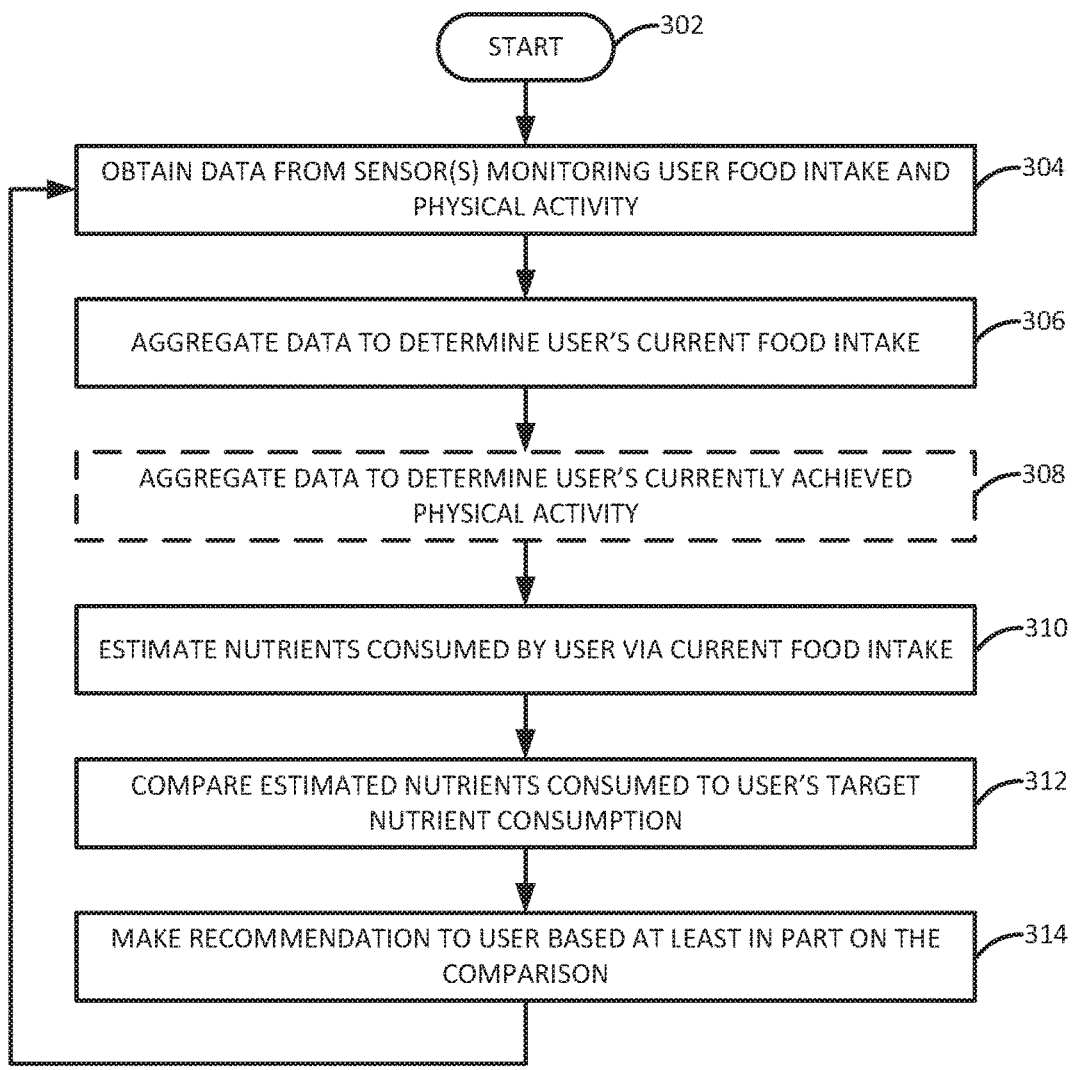
FIG. 3 illustrates a flowchart of a first example method for monitoring a user's food intake.

FIG. 3 illustrates a flowchart of a first example method 300 for monitoring a user's food intake. In one example, the method 300 may be performed by a mobile device such as a mobile phone or wearable smart device, e.g., one of the user endpoint devices 108, 110, 112, or 114 illustrated in FIG. 1. However, in other examples, the method 300 may be performed by another device, such as the AS 104 of FIG. 1. As such, any references in the discussion of the method 300 to the user endpoint devices 108, 110, 112, and 114 of FIG. 1 are not intended to limit the means by which the method 300 may be performed.

The method 300 begins in step 302. In step 304, data is obtained (e.g., by the AS 104 or by the user endpoint devices 108, 110, 112, or 114) from one or more sensors (e.g., sensors 116, 118, 120, and/or 122). In one example, the data is extracted from a series of packets sent over a network (e.g., network 100) by the sensors. In one example, the data relates to a user's food intake. For instance, the data may comprise information about food that has been consumed by the user. Food intake may also include the consumption of vitamin supplements (e.g., multivitamins, iron or fish oil supplements, etc.). As an example, the data may comprise an image of the food, information extracted from a machine readable label attached to the food, a reading from a temperature or pressure sensor attached to a plate or utensil used to consume the food or an appliance used to store or prepare the food, an input made by the user to a nutrition or fitness tracking application, or other data. In a further example, the data may also relate to the user's physical activity. For instance, the data may comprise a reading from a wearable fitness tracker, a reading from a scale, an input made by the user to a nutrition or fitness tracking application, or other data. In one example, data is sent by the sensors on a continuous basis, e.g., in substantially real time (subject to any network latency) as the data is collected by the sensors.

In step 306, the data obtained in step 304 is aggregated (e.g., by the AS 104 or by the user endpoint devices 108, 110, 112, or 114) to determine the user's current food intake. For instance, if the data included an image of a piece of fish, a reading from a pressure sensor attached to the plate on which the fish was placed that indicated a weight of eight ounces, and a reading from a temperature sensor indicating that the temperature of the cooked fish is approximately 450 degrees Fahrenheit, then it may be estimated that the user consumed eight ounces of slightly overcooked fish (where the overcooking may have led to some breakdown in some of the nutrients). In further examples, the type of fish consumed may also be estimated (e.g., from the image or from a machine readable label affixed to packaging). In one example, a recognition process (e.g., character recognition, object recognition, text recognition, or speech recognition) is employed to extract meaning from the data obtained in step 304 (e.g., to determine what type of food is depicted in an image, what information is contained on a nutritional label, etc.).

In optional step 308 (illustrated in phantom), the data obtained in step 304 is aggregated (e.g., by the AS 104 or by the user endpoint devices 108, 110, 112, or 114) to determine the user's current level of physical activity achieved. For instance, the data may include a reading from a wearable fitness tracker indicating that the user burned a certain amount of calories or walked a certain number of steps between waking up and the present time.

In step 310, the nutrients consumed via the current food intake are estimated (e.g., by the AS 104 or by the user endpoint devices 108, 110, 112, or 114). For example, if it is determined in step 306 that the user consumed eight ounces of salmon, then it may be estimated that the eight ounces of salmon contained approximately 470 calories, 45 grams of protein, 125 milligrams of cholesterol, and the like. In one example, a database storing nutritional information for a variety of foods (e.g., DB 106) may be queried to estimate the nutrients consumed, based on knowledge of the food intake as determined in step 306.

In step 312, the nutrients consumed via the current food intake are compared (e.g., by the AS 104 or by the user endpoint devices 108, 110, 112, or 114) to a target nutrient consumption for the user to determine whether there are any shortfalls in particular nutrients (e.g., not enough iron), or alternatively whether the user has consumed particular nutrients in excess of the target nutrient consumption (e.g., too much sodium). For instance, if the user's target protein consumption for a day is 50 grams, and his current food intake has resulted in a consumption of 45 grams of protein, it may be determined that the user should consume at least an additional 5 grams of protein before the end of the day to consume a target amount of protein. In one example, the comparison of nutrients consumed versus target nutrient consumption may further account for any nutrients that may have been lost via physical activity, e.g., as determined in step 308. For instance, calories burned or electrolytes lost due to exercise may offset the nutrients that are estimated to have been consumed via the current food intake.

In step 314, a recommendation is made (e.g., by the AS 104 or by the user endpoint devices 108, 110, 112, or 114) to the user, based at least in part on the comparison performed in step 310, to assist the user in consuming optimal (e.g., target) nutrients. The recommendation may be sent, for example, to the user's mobile device (e.g., by the AS 104 to one of the user endpoint devices 108, 110, 112, or 114) in the form of a visual alert (e.g., text message or application-based alert) and/or an audible alert (e.g., synthesized speech or pre-recorded message). The recommendation may suggest any one or more of: a specific amount of a specific nutrient that should be consumed to meet the target nutrient consumption or minimize a shortfall in the target nutrient consumption (e.g., 5 grams of protein), a specific nutrient whose consumption should be at least temporarily reduced (e.g., approaching target sodium consumption), a specific food or amount of food that can be consumed to meet the target nutrient consumption (e.g., 25 grams of almonds, eight ounces of water, etc.), a specific food or amount of food that can be consumed to minimize a further increase in a nutrient that has been consumed in excess, or a recipe for preparing a specific meal that can be consumed to meet the target nutrient consumption. In a further example, the recommendation may include a coupon, advertisement, or hyperlink to purchase a suggested food. The suggested food could be a food that the user can consume more of to meet a target nutrient consumption, a food that the user is observed consuming frequently, or an alternative to a food that the user is observed consuming frequently.

In a further example still, the recommendation may include an autonomous action taken without direct user instruction, such as automatically placing an order to purchase groceries when the user's supply of a certain food in the refrigerator is observed to be low or of diminishing quality (e.g., need more milk, yogurt is expired, strawberries look mushy, etc.). Such actions may be taken in accordance with user preferences stored in a database (e.g., DB 106). The preferences may indicate, for instance, preferred brands for particular kinds of foods, preferred vendors from which to purchase food, how low to let the current supply of a particular food reach before placing an order to replenish, how frequently to "shuffle" the contents of the refrigerator (e.g., move items around to increase and/or decrease visibility or accessibility), etc.

The method 300 then returns to step 304 and proceeds as described above to continue monitoring the user's food intake and making recommendations, until instructed to stop (e.g., by the user).

Further examples of the present disclosure may include sensors that cooperate with appliances or devices to assist in meal preparation. For instance, smart appliances (e.g., an ice maker in a refrigerator) could be instructed to take a certain action (e.g., make ice) in anticipation of a particular food being prepared (e.g., a smoothie). In another example, sensors in the refrigerator may communicate the contents of the refrigerator to a user endpoint device or to an application server, which may in turn query a database for recipes that can be prepared using the contents of the refrigerator. These recipes could then be recommended to the user.

Although not expressly specified above, one or more steps of the method 300 may include a storing, displaying and/or outputting step as required for a particular application. In other words, any data, records, fields, and/or intermediate results discussed in the method can be stored, displayed and/or outputted to another device as required for a particular application. Furthermore, operations, steps, or blocks in FIG. 3 that recite a determining operation or involve a decision do not necessarily require that both branches of the determining operation be practiced. In other words, one of the branches of the determining operation can be deemed as an optional step. Furthermore, operations, steps or blocks of the above described method(s) can be combined, separated, and/or performed in a different order from that described above, without departing from the examples of the present disclosure.

FIG. 4 depicts a high-level block diagram of a computing device specifically programmed to perform the functions described herein. For example, any one or more components or devices illustrated in FIG. 1 or described in connection with the method 300 may be implemented as the system 400.

For instance, a user endpoint device (such as any of the UEs 108, 110, 112, or 114 of FIG. 1, or the device 200 of FIG. 2) or an application server (such AS 104 of FIG. 1) could be implemented as illustrated in FIG. 4.

As depicted in FIG. 4, the system 400 comprises a hardware processor element 402, a memory 404, a module 405 for monitoring food intake, and various input/output (I/O) devices 406.

The hardware processor 402 may comprise, for example, a microprocessor, a central processing unit (CPU), or the like. The memory 404 may comprise, for example, random access memory (RAM), read only memory (ROM), a disk drive, an optical drive, a magnetic drive, and/or a Universal Serial Bus (USB) drive. The module 405 for monitoring food intake may include circuitry and/or logic for performing special purpose functions relating to the monitoring, reporting, and providing feedback relating to a user's food intake. The input/output devices 406 may include, for example, a camera, a video camera, storage devices (including but not limited to, a tape drive, a floppy drive, a hard disk drive or a compact disk drive), a receiver, a transmitter, a speaker, a microphone, a transducer, a display, a speech synthesizer, an output port, and a user input device (such as a keyboard, a keypad, a mouse, and the like), a health-related sensor (e.g., a glucose monitor, a heart rate monitor, a blood pressure monitor, or a blood alcohol monitor), or another type of sensor.

Although only one processor element is shown, it should be noted that the general-purpose computer may employ a plurality of processor elements. Furthermore, although only one general-purpose computer is shown in the Figure, if the method(s) as discussed above is implemented in a distributed or parallel manner for a particular illustrative example, i.e., the steps of the above method(s) or the entire method(s) are implemented across multiple or parallel general-purpose computers, then the general-purpose computer of this Figure is intended to represent each of those multiple general-purpose computers. Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented.

It should be noted that the present disclosure can be implemented in software and/or in a combination of software and hardware, e.g., using application specific integrated circuits (ASIC), a programmable logic array (PLA), including a field-programmable gate array (FPGA), or a state machine deployed on a hardware device, a general purpose computer or any other hardware equivalents, e.g., computer readable instructions pertaining to the method(s) discussed above can be used to configure a hardware processor to perform the steps, functions and/or operations of the above disclosed method(s). In one example, instructions and data for the present module or process 405 for monitoring food intake (e.g., a software program comprising computer-executable instructions) can be loaded into memory 404 and executed by hardware processor element 402 to implement the steps, functions or operations as discussed above in connection with the example method 300. Furthermore, when a hardware processor executes instructions to perform "operations," this could include the hardware processor performing the operations directly and/ or facilitating, directing, or cooperating with another hardware device or component (e.g., a co-processor and the like) to perform the operations.

The processor executing the computer readable or software instructions relating to the above described method(s) can be perceived as a programmed processor or a specialized processor. As such, the present module 405 for monitoring food intake (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. More specifically, the computer-readable storage device may comprise any physical devices that provide the ability to store information such as data and/or instructions to be accessed by a processor or a computing device such as a computer or an application server.

While various examples have been described above, it should be understood that they have been presented by way of example only, and not limitation. Thus, the breadth and scope of a preferred example should not be limited by any of the above-described examples, but should be defined only in accordance with the following claims and their equivalents.

What is claimed is:

1. A method, comprising:
monitoring, by at least one processor, a food intake of a user based on data collected from at least one sensor, wherein the data comprises an image of a food item consumed by the user and a reading from a pressure sensor attached to a plate on which the food item consumed by the user is placed;
estimating, by the at least one processor, a current nutrient consumption of the user based on the monitoring, wherein the estimating comprises:
aggregating the data to determine an identity and a quantity of the food item consumed by the user, wherein the identity comprises an identification of the food item consumed by the user; and
based on the aggregating, determining a nutritional content of the food item consumed by the user; and
presenting, by the at least one processor, a recommendation to the user based on the estimating, wherein the recommendation is designed to help the user achieve a target nutrient consumption, wherein the recommendation comprises a recipe for preparing another food item to be consumed by the user for meeting the target nutrient consumption, wherein the target nutrient consumption comprises at least one of: a target carbohydrate consumption, a target protein consumption, a target lipid consumption, a target vitamin consumption, or a target mineral consumption.

2. The method of claim 1, wherein the data further comprises information extracted from a machine readable label attached to the food item consumed by the user.

3. The method of claim 1, wherein the data comprises a reading from a temperature sensor attached to the plate, a cup, or a utensil used by the user to consume the food item consumed by the user.

4. The method of claim 1, wherein at least one of the at least one sensor is integrated in a user endpoint device used by the user.

5. The method of claim 1, wherein at least one of the at least one sensor is integrated in an appliance used to prepare the food item consumed by the user.

6. The method of claim 1, wherein at least one of the at least one sensor is integrated in an appliance used to store the food item consumed by the user.

7. The method of claim 1, wherein at least one of the at least one sensor is integrated in an item used to consume the food item consumed by the user.

8. The method of claim 1, further comprising:
aggregating the data to determine a current level of physical activity achieved by the user; and
offsetting the current nutrient consumption based on the current level of physical activity.

9. The method of claim 1, wherein the recommendation is generated by:
comparing the current nutrient consumption to the target nutrient consumption;
detecting a shortfall in a particular nutrient, based on the comparing; and
identifying the another food item that can be consumed by the user to minimize the shortfall.

10. The method of claim 1, wherein the recommendation is generated by:
comparing the current nutrient consumption to the target nutrient consumption;
detecting an excess in a particular nutrient, based on the comparing; and
identifying the another food item that can be consumed by the user to minimize a further increase in the particular nutrient.

11. The method of claim 1, wherein the recommendation further includes at least one of: an advertisement for the another food item, a hyperlink to purchase the another food item, or automatically placing an order to purchase groceries.

12. The method of claim 1, wherein the current nutrient consumption comprises at least one of: a current carbohydrate consumption, a current protein consumption, a current lipid consumption, a current vitamin consumption, or a current mineral consumption.

13. A device, comprising:
a processor; and
a computer-readable medium storing instructions which, when executed by the processor, cause the processor to perform operations, the operations comprising:
monitoring a food intake of a user based on data collected from a sensor, wherein the data comprises an image of a food item consumed by the user and a reading from a pressure sensor attached to a plate on which the food item consumed by the user is placed;
estimating a current nutrient consumption of the user based on the monitoring, wherein the estimating comprises:
aggregating the data to determine an identity and a quantity of the food item consumed by the user, wherein the identity comprises an identification of the food item consumed by the user; and
based on the aggregating, determining a nutritional content of the food item consumed by the user; and
presenting a recommendation to the user based on the estimating, wherein the recommendation is designed to help the user achieve a target nutrient consumption, wherein the recommendation comprises a recipe for preparing another food item to be consumed by the user for meeting the target nutrient consumption, wherein the target nutrient consumption comprises at least one of: a target carbohydrate consumption, a target protein consumption, a target lipid consumption, a target vitamin consumption, or a target mineral consumption.

14. The device of claim 13, wherein the data further comprises information extracted from a machine readable label attached to the food item consumed by the user.

15. The device of claim 13, wherein the data comprises a reading from a temperature sensor attached to the plate, a cup, or a utensil used by the user to consume the food item consumed by the user.

16. An apparatus, comprising:
a sensor to detect information about a food item placed in the apparatus;
a processor to evaluate the information detected by the sensor and to generate a recommendation regarding a preparation of the food item, based on the information, by:
aggregating the information to determine an identity and a quantity of the food item, wherein the identity comprises an identification of the food item; and
based on the aggregating, determining a nutritional content of the food item; and
a user interface to present the recommendation to a user regarding the preparation of the food item by the apparatus, wherein the recommendation is designed to help the user achieve a target nutrient consumption, wherein the recommendation comprises a recipe for preparing another food item to be consumed by the user for meeting the target nutrient consumption, wherein the target nutrient consumption comprises at least one of: a target carbohydrate consumption, a target protein consumption, a target lipid consumption, a target vitamin consumption, or a target mineral consumption.

17. The apparatus of claim 16, wherein the apparatus is a microwave oven, and the sensor is an imaging sensor on a door of the microwave oven.

18. The apparatus of claim 16, wherein the apparatus is a microwave oven and the sensor is a pressure sensor mounted on a tray of the microwave oven.

19. The apparatus of claim 16, wherein the recommendation is generated by:
comparing a current nutrient consumption of the user to the target nutrient consumption;
detecting a shortfall in a particular nutrient, based on the comparing; and
identifying the another food item that can be consumed by the user to minimize the shortfall.

20. The apparatus of claim 16, wherein the nutritional content of the food item comprises at least one of: a carbohydrate content, a protein content, a lipid content, a vitamin content, or a mineral content.

* * * * *